(12) United States Patent
Chantara et al.

(10) Patent No.: US 6,485,759 B2
(45) Date of Patent: Nov. 26, 2002

(54) BOTANICAL COMBINATIONS FOR TREATING AIDS AND IMMUNE-DEFICIENT PATIENTS TO MAINTAIN GOOD HEALTH AND THE PROCESS FOR PREPARING THE SAME

(75) Inventors: Kim Chantara, Bangkok (TH); Krisana Kraisintu, Bangkok (TH)

(73) Assignee: The Government Pharmaceutical Organization Research and Development Institute, Bangkok (TH)

( * ) Notice: Subject to any disclaimer, the term of this patent is extended or adjusted under 35 U.S.C. 154(b) by 0 days.

(21) Appl. No.: 09/905,597

(22) Filed: Jul. 12, 2001

(65) Prior Publication Data

US 2002/0006446 A1 Jan. 17, 2002

Related U.S. Application Data

(63) Continuation-in-part of application No. 09/613,105, filed on Jul. 10, 2000, now abandoned, which is a continuation-in-part of application No. 08/977,501, filed on Nov. 24, 1997, now abandoned.

(51) Int. Cl.[7] .................. A01N 65/00; A61K 47/00; A61K 9/64; A61K 9/48; A61K 35/78
(52) U.S. Cl. ................. 424/756; 424/439; 424/452; 424/465; 424/469; 424/492; 424/725
(58) Field of Search ............... 424/725, 195.1, 424/439, 464, 452, 456, 465, 469, 492

(56) References Cited

U.S. PATENT DOCUMENTS

| | | | |
|---|---|---|---|
| 4,618,495 A | | 10/1986 | Okuda et al. |
| 5,494,667 A | * | 2/1996 | Uchida et al. |
| 5,529,778 A | | 6/1996 | Rohatgi |
| 6,264,926 B1 | * | 7/2001 | Farooqi et al. |

FOREIGN PATENT DOCUMENTS

JP    57-212123    12/1982

OTHER PUBLICATIONS

Perry CM and Noble S Drugs (1999), 58(6), 1099–1130.
Singh N, et al. Arch Intern Med (1996), 156(2), 197–201.
Fact Sheet—UPJOHN 0021 McKinley GF; http://va.evolvingtech.com/ Jan. 29, 2001.
Medical Considerations–Karnofsky Performance Scale:http://www.hivdent.org/ Jan. 29, 2001.

* cited by examiner

Primary Examiner—Herbert J. Lilling
(74) Attorney, Agent, or Firm—S. Jesadanont

(57) ABSTRACT

Botanical Combination therapies for treating AIDS and immune-deficient patients include therapeutically effective doses of five medicinal plants of Thailand. First combination, ayurvedic composition 1, consists of ground and spray-dried plant extracts *Houttuynia cordata, Combretum quadrangulare, Mimusops elengi, Randia siamensis*, and *Borassus flabellifer* in the varied amount. Drug mixture is administered one capsule twice daily. Second combination therapy consists of ayurvedic composition 1 (one capsule twice daily) plus one capsule of ayurvedic composition 2 twice daily. Ayurvedic composition 2 is powder of *Houttuynia cordata* extract in varied amounts. Ayurvedic composition 3 consists of dried extracts of five plant materials in fixed amounts. Ayurvedic composition 4 is dried extract of *Houttuynia cordata* 100 mg. A process for preparing includes washing, drying and grinding the plant materials into powder, extracting by boiling, filtering, drying the extract, mixing dried extracts in varied or defined amount and preparing pharmaceutical dosage forms of plant extract mixture.

8 Claims, No Drawings

BOTANICAL COMBINATIONS FOR TREATING AIDS AND IMMUNE-DEFICIENT PATIENTS TO MAINTAIN GOOD HEALTH AND THE PROCESS FOR PREPARING THE SAME

CROSS-REFERENCE TO RELATED APPLICATION

This is a continuation-in-part of application Ser. No. 09/613,105, filed Jul. 10, 2000, now abandoned which is a continuation-in-part of application Ser. No. 08/977,501, filed Nov. 24, 1997, now abandoned whose contents are hereby incorporated.

FIELD OF THE INVENTION

This invention pertains to herbal extracts, formulations and method for preparing the botanical combinations which can be used for treating AIDS and immune-deficient patients to maintain Kamofsky performance status greater than or equal to 90.

DESCRIPTION OF THE BACKGROUND ART

The currently accepted theory of Acquired Immune Deficiency Syndrome (AIDS) involves the loss of the helper cells of the immune system due to infection with the Human Immunedeficiency Virus (HIV). In the advanced stages of the disease, the immune system is rendered helpless in resisting even the normal bacterial flora encountered every day. Eventually, the patient is overcome by bacterial, fungal and viral infections and dies as a result of these opportunistic infections.

Considerable research, therefore, has been aimed at developing synthetic drugs that inhibit one or more stages of the viral life cycle of HIV. Limited success has been achieved by inhibiting the virus-coded reverse transcriptase and protease enzymes. However, a cure for AIDS has not yet been found, and therapy using the nucleoside analogs, although is used currently, has been limited due to many toxic side effects.

While many of the presently synthetic drugs inhibit one or more stages of the viral life cycle of viruses, only a few agents have had any practical value as stated in many pharmacopoeia and textbooks that the specific therapy for viral infections are generally unsatisfactory and thus treatment is primarily symptomatic. Moreover, many of these synthetic drugs show serious systemic adverse effects on various tissues to deteriorate the health even of a normal person. This is also the main reason why a large number of patients currently turn to traditional drugs where the partially purified drug contains mixture of ingredients helps not only suppressing certain pathogenic agents but also promote the well-being of a person that the appetite and body weight are in well-balance. This advantages of traditional drugs are presently realized world-wide and have now been proofed and used clinically especially in Europe, China and many other countries even the real mechanism of action can not yet be delineated.

Thus, there has been a revival in the use of traditional medicine to treat modern disease worldwide. The major source of traditional medicine is in developing countries in which large portions of the populations still rely heavily on indigenous traditional practitioners and local medicinal plants for satisfying their primary health care needs which is, in general, quite self-sufficient. Remedies making use of crude plant materials or their extracts have been handed down through many generations and kept largely secret by traditional practitioners. Continuing efforts to document these formulations are necessary to preserve this information which presently revealed invaluable. Attempts have also been made to improve the formula to give the best therapeutic results.

Herbal remedies have three main advantages over modern synthetic drugs. The first is that their long term use already establishes a certain degree of safety and efficacy in the use of the plant material for human consumption. The second advantage arises out of the use of crude plant materials, which are less costly to prepare than the isolated or synthetic medicinal compounds. In these crude plant materials with many natural components, several compounds in the plant very often act synergistically to increase the effectiveness of the crude plant preparation compared to isolated compounds. The third advantage of the use of medicinal plants is a reduced incidence of adverse drug reactions common to most therapies utilizing synthetic drugs.

The present invention describes formulation and process of making botanical compositions for maintaining Karnofsky score (KS) of 90–100 in immune-deficient patients and especially in AIDS patients. The formulated composition helps maintaining Kamofsky Score (KS) or Kamofsky Performance Scale ranges 90–100 of AIDS patients (vs 100 as of a normal person) with a mean CD4 count of 420 over a 100-week period with slight increase in body weight, where some patients even gain weight significantly. A follow-up result at 100 weeks after treatment using botanical combinations of the present invention shows that all patients are free of opportunistic infections, without undesirable adverse effects and new AIDS-defining event including no developing AIDS dementia complex or other cerebral events and can live a normal life. This is due to the fact that some of the herbal components possesses anti-infectious activity while some has appetite stimulatory effect. These botanical combinations help maintaining Kamofsky score (KS) of 90–100 in all AIDS patients being on the regimen over a 100-week non-comparative clinical trial period although the CD4 count has been shown to increase in only some patients (11 out of 25). This is in great contrast to those patients using didanosine 375 or 250 mg twice daily (for patients weighing <60 kg, n=279) and zidovudine 12 mg/kg/day (n=275) where 73% of patients in each group had experienced a new AIDS-defining event and 40% of patients in each group had died after 80 weeks of treatment (Perry and Noble, 1999). In addition, the cost of the presently described regimen is considerable inexpensive and affordable by the patients. These are contrary to those AIDS patients on very expensive modem regimens whose serious toxic side effects especially bone marrow suppression, abdominal pain, pancreatitis and peripheral neuropathy or lactic acidosis with hepatic steatosis are often the main cause of patient mortality (30–50% ) within a year after starting the therapy despite the fact that reduction in HIV viral load and plasma HIV RNA level have been reported.

BRIEF SUMMARY OF THE INVENTION

Botanical Combination therapies for maintaining Kamofsky score (KS) of 90–100 in AIDS and immune-deficient patients include therapeutic doses of five medicinal plants of Thailand. The first combination drug, ayurvedic composition 1, consists of spray-dried aqueous or aqueous organic solvent extracts of the plant materials *Houttuynia cordata, Combretum quadrangulare, Mimusops elengi, Randia siamensis,* and *Borassus flabellifer* in varied amounts 10–300 mg, 10–100 mg, 10–100 mg, 10–100 mg, and 60–600 mg, respectively. The drug mixture is administered in the form of one capsule (100–1,200 mg) twice daily. The second combination therapy consists of ayurvedic composition 1 (one capsule twice daily) plus one 10–500 mg capsule of ayurvedic composition 2 twice daily, where ayurvedic composition 2 is lyophilized or spray-dried powder of aqueous or aqueous organic solvent extract of plant *Houttuynia cordata* 10–500 mg. Ayurvedic composition 3 consists of dried aqueous or aqueous organic solvent extracts of the plant materials *Houttuynia cordata, Combretum quadrangulare, Mimusops elengi, Randia siamensis*, and *Borassus flabellifer* in fixed amounts 32 mg, 20 mg, 20 mg, 20 mg, and 400 mg, respectively. Ayurvedic composition 4 is lyophilized or spray-dried powder of aqueous or aqueous organic solvent extract of plant material *Houttuynia cordata* in fixed amount, 100 mg. A process for preparing the botanical combinations includes washing, drying and grinding plant materials into powder, extracting the powder by boiling in water, filtering, spray-drying the extract and mixing the dried extracts in defined amount. The process also includes preparing the pharmaceutical dosage forms of the plant extract mixture as hard gelatin capsule which is stored in air-tight containers protected from light and as syrup or tablet or the like.

DETAILED DESCRIPTION OF THE INVENTION

The therapy presented here for maintaining Kamofsky score (KS) of 90–100 in AIDS and immune-deficient patients makes use of the combinations of botanical drugs. As Kamofsky Score (KS) or Kamofsky Performance Scale is currently accepted to be used in assessment protocols for evaluating an effect of herbal remedy in clinical management of the HIV/AIDS patient as primary end point representing the Degree of Quality of Life (http://www.hivdent.org), the term 'good health' of the patients referred to in the present description means that such person has been evaluated to have Karnofsky performance status greater than or equal to 90 as he is normal and no complaints, with no evidence of disease or is able to carry on normal activity with minor signs and symptoms of disease. The first is a combination of medicinal plant extracts in measured proportions, ayurvedic composition 1, and the second is a single medicinal plant, ayurvedic composition 2. Ayurvedic composition 1 can be given with or without ayurvedic composition 2, depending on the patient condition. This combination therapy acts by inhibiting opportunistic infections with concurrent stinulation of the immune system. By increasing the body's ability to fight against various infectious microorganisms, the symptoms associated with AIDS are suppressed or eliminated.

This invention consists of a botanical combination of plant materials, ayurvedic composition 1, in capsule form, as well as a single botanical drug, ayurvedic composition 2, to be used for the purpose of maintaining Karnofsky score (KS) of 90–100 reflecting good health in AIDS and immune-deficient patients, and the process for preparing the same.

This invention, including the aqueous or aqueous organic solvent extracts of *Houttuynia cordata, Combretum quadrangulare, Mimusops elengi, Randia siamensis*, and *Borassus flabellifer*, is used for treating to maintain Karnofsky score (KS) of 90–100 in AIDS and immune-deficient patients.

All five plants are grown and harvested all year round where from the three plants, *Combretum quadrangulare, Mimusops elengi*, and *Randia siamensis*, stems and branches are used; while the whole plant of *Houttuynia cordata* and inflorescences of *Borassus flabellifer* are used. The parts of plant to be used are dried at 60 degree Celsius until constant dry weight is obtained. Each dry ingredient is ground and put through a sieve to obtain powder of uniform particle size. Water is added to cover the powder using approximately 70 liters for 10 Kg dry weight of powder and the mixture is heated until boils for five minutes and simmered at 80 degree Celsius for the next 8 hr. The filtrate is collected and the residual powder is further boiled in 50 liters water and simmered in similar manner twice. All three filtrates are pooled and spray-dried, freeze-dried or concentrating-dried to obtain dried powder extract of each ingredient referred to as dried plant extract. Alternatively, aqueous organic solvent such as ethyl alcohol may also be used instead of water. A similar extraction process is used to extract each plant ingredient to give all the dried plant extracts used in the present invention. The constituents in the dried plant extract of each plant are identified and quantitatively analysed using conventional High Performance Liquid Chromatography. The same method is used to quantify the amount of each plant constituent to be mixed in the pharmaceutical preparations. Furthermore, since the weather does not vary much during the year in the country of plant origin, i.e.—Thailand, where these plants are grown and harvested, there is thus not much difference between the crops harvested at different time of the year regarding the quality and the quantity of the constituents of each plant.

The formulations consist of the following proportions of each plant material:

(i) ayurvedic composition 1 consisting of the dried plant extracts of:

| | |
|---|---|
| *Houttuynia cordata* | 10–300 mg |
| *Combretum quadrangulare* | 10–300 mg |
| *Mimusops elengi* | 10–300 mg |
| *Randia siamensis* | 10–300 mg |
| *Borassus flabellifer* | 60–600 mg |
| Total weight of one capsule | 100–1,200 mg | and (ii) ayurvedic composition 2 consisting of the lyophilized or spray-dried powder of aqueous or aqueous organic solvent extract of plant material in the amount:
*Houttuynia cordata* 10–500 mg This invention further relates to the process for preparing the said botanical mixture for maintaining Karnofsky score (KS) of 90–100 in AIDS and immune-deficient patients. The process consists of washing the plant materials *Houttuynia cordata, Combretum quadrangulare, Mimusops elengi, Randia siamensis* and *Borassus flabellifer* with water to remove external contaminants, followed by drying and grinding into powder form each of the said botanicals. The powdered materials are then extracted with water or aqueous organic solvent, spray-dried, freeze-dried or concentrating-dried, and then mixed in the following proportions:

(i) ayurvedic composition 1 consisting of dried plant extracts in the amounts:

| | |
|---|---|
| *Houttuynia cordata* | 10–300 mg |
| *Combretum quadrangulare* | 10–300 mg |
| *Mimusops elengi* | 10–300 mg |
| *Randia siamensis* | 10–300 mg |

| -continued | |
|---|---|
| *Borassus flabellifer* | 60–600 mg |
| Total weight of one capsule | 100–1,200 mg |

(ii) ayurvedic composition 2 consisting of the lyophilized or spray-dried powder of aqueous or aqueous organic solvent extract of plant material in the amount:
   *Houttuynia cordata* 10–500 mg
and prepared as pharmaceutical dosage forms.

The total amount of each pharmaceutical dosage form is 100–1,200 mg of the extracts of the said botanical mixture, ayurvedic composition 1, and 10–500 mg of the single botanical drug, ayurvedic composition 2. Both drugs are in the form of hard gelatin capsules. The capsules are stored protected from light in plastic or glass containers with silica gel bags as desiccant, and the openings of the containers are sealed with aluminum foil.

Dosage

One capsule of ayurvedic composition 1 contains the dried extracts of the aforesaid botanicals with a total weight of 100–1,200 mg, and the dosage is one capsule twice daily. One capsule of ayurvedic composition 2 contains 10–500 mg of washed, lyophilized or spray-dried powder of aqueous or aqueous organic solvent extract of plant material *Houttuynia cordata*, and the dosage is one capsule twice daily. Both dosages may vary according to each individual patient and the advice of a physician.

The presence of HIV in patients' blood is confirmed by the Elisa and Western Blot assays. Full blown AIDS patients are further identified by the common symptoms of AIDS including the presence of opportunistic infections. The CD4 (helper cells), total lymphocytes, and weight of the patients are monitored during therapy; in addition to performing liver function tests (LFT) and general blood chemistry tests.

One capsule of ayurvedic composition 1 is administered twice daily to confirmed cases of full blown AIDS or HIV positive patients. Ayurvedic composition 2, in the dosage of one capsule twice daily is also given to patients with evidence of TB or opportunistic fungal, viral or bacterial infections. A successful therapy will result in the disappearance of symptoms within three weeks (i.e. disappearance of opportunistic infections), as well as stabilization of body weight. Treatment is then continued to maintain body weight and prevent the return of the symptoms of AIDS. Patients are also given a regimen of multivitamins to ensure proper nutrition.

The dosage may vary according to the advice of a physician. Patients are prohibited from taking any drugs which suppress the immune system; immunesuppressive drugs are contraindicated.

EXAMPLE 1

Preparation of Dosage Forms

The preparation of the botanical drugs for maintaining Karnofsky score (KS) of 90–100 in AIDS and immune-deficient patients consists of washing the plant materials *Houttuynia cordata, Combretum quadrangulare, Mimusops elengi, Randia siamensis* and *Borassus flabellifer* with water to remove external contaminants, followed by drying and grinding into powder form each of the said botanicals. The powdered materials are then extracted with water or aqueous organic solvent comprising 5–80% v/v of a water miscible organic solvent, preferably ethanol. The extracts are dried by the drying means such as spray-drying or freeze-drying or concentrating-drying. The powder obtained are mixed in the following proportions to yield ayurvedic composition 3, consisting of dried plant extracts in fixed amounts:

| *Houttuynia cordata* | 32 mg |
|---|---|
| *Combretum quadrangulare* | 20 mg |
| *Mimusops elengi* | 20 mg |
| *Randia siamensis* | 20 mg |
| *Borassus flabellifer* | 308 mg |
| Total weight of one capsule | 400 mg |

The botanical drug ayurvedic composition 4 is prepared using the lyophilized or spray-dried powder of aqueous or aqueous organic solvent extract of plant material *Houttuynia cordata* in fixed amount:
   *Houttuynia cordata* 100 mg The two drugs, ayurvedic composition 3 and ayurvedic composition 4, each are then filled into hard gelatin capsules. The total weight of the powdered plant extract mixture in one ayurvedic composition 3 capsule is 400 mg, whereas the total weight of *Houttuynia cordata* powdered plant material in one ayurvedic composition 4 capsule is 100 mg. The capsules are stored protected from light in plastic or glass containers with silica gel bags, and the openings of the containers are sealed with aluminum foil.

EXAMPLE 2

Botanical Mixture: ayurvedic composition 3

This botanical combination drug, ayurvedic composition 3, for maintaining Karnofsky score (KS) of 90–100 in AIDS and immune-deficient patients consists of a mixture of dried plant extracts in the amounts:

| *Houttuynia cordata* | 32 mg |
|---|---|
| *Combretum quadrangulare* | 20 mg |
| *Mimusops elengi* | 20 mg |
| *Randia siamensis* | 20 mg |
| *Borassus flabellifer* | 308 mg |
| Total weight of one capsule | 400 mg |

The total weight of one capsule of ayurvedic composition 3 is 400 mg. The usual dose is one capsule twice daily.

Each plant material is washed with water to remove external contaminants, dried, and ground into a powder. The powdered plant materials are then extracted with water or aqueous organic solvent comprising 5–80% v/v of a water miscible organic solvent, preferably ethanol. The extracts are dried by the drying means such as spray-drying or freeze-drying or concentrating-drying. The combination drug ayurvedic composition 3 is prepared by mixing the dried plant extracts in the said proportions and filled into hard gelatin capsules, which are then stored in glass or plastic containers with silica gel bags and sealed with aluminum foil.

EXAMPLE 3

Botanical Mixture: Ayurvedic Composition 3 Plus Ayurvedic Composition 4

This botanical combination drug for maintaining Karnofsky score (KS) of 90–100 in AIDS and immune-deficient patients comprises:

(i) ayurvedic composition 3 consisting of dried plant extracts in fixed amounts:

| *Houttuynia cordata* | 32 mg |
|---|---|
| *Combretum quadrangulare* | 20 mg |
| *Mimusops elengi* | 20 mg |

-continued

| | |
|---|---|
| *Randia siamensis* | 20 mg |
| *Borassus flabellifer* | 308 mg |
| Total weight of one capsule | 400 mg | and (ii) ayurvedic composition 4 consisting of the lyophilized or spray-dried powder of aqueous or aqueous organic solvent extract of plant material *Houttuynia cordata* in fixed amount:

*Houttuynia cordata* 100 mg

The total weight of one capsule of ayurvedic composition 3 is 400 mg, and the total weight of one capsule of ayurvedic composition 4 is 100 mg. The usual dose is one capsule of ayurvedic composition 4 twice daily in addition to one capsule of ayurvedic composition 3 twice daily (i.e. one capsule of each drug twice daily).

Each plant material is washed with water to remove external contaminants, dried, and ground into powder. The combination drug ayurvedic composition 3 is prepared by mixing the dried extracts of the said plant materials in the said proportions and filled into hard gelatin capsules, which are then stored protected from light in glass or plastic containers with silica gel bags and sealed with aluminum foil. The botanical drug ayurvedic composition 4 is prepared by filling hard gelatin capsules with the lyophilized or spray-dried extract of plant material *Houttuynia cordata* 100 mg, and packaged protected from light in glass or plastic containers with silica gel bags and sealed with aluminum foil.

EXAMPLE 4
The Adjuvant Drug Ayurvedic Composition 4

This adjuvant drug for maintaining Karnofsky score (KS) of 90–100 in AIDS and immune-deficient patients comprises: ayurvedic composition 4, consisting of 100 mg of the lyophilized or spray-dried extract of plant material *Houttuynia cordata* in capsule form. The usual dose is one capsule of ayurvedic composition 4 twice daily as an adjuvant therapy to treat opportunistic infections. The plant material and pharmaceutical dosage form is prepared as mentioned above.

In some cases, the single drug may be prepared by using the washed, lyophilized and ground plant material, *Houttuynia cordata*, in variable amounts 10–500 mg or in fixed amount 100 mg, which are shown to give equivalent therapeutic effects.

In all cases and examples, the botanical combination(s) may be also prepared in any other pharmaceutical dosage forms currently available such as syrup or tablet or any other forms which is therapeutically effective and convenient for administration in AIDS and immune-deficient patients.

Table 1 shows therapeutic effect of the botanical combinations ayurvedic composition 3 used singly or together with ayurvedic composition 4 in maintaining body weight and Karnofsky Performance Scale of 90–100 of AIDS patients in a 100-week noncomparative clinical study. All patients remained healthy, free of opportunistic infections, no developing AIDS dementia complex or other cerebral events and free of moderate or serious adverse effects commonly observed in antiretroviral therapy where no new AIDS-defining events and no mortality has been observed. This is in contrast to the use of synthetic antiretroviral drug where in patients treated with didanosine 375 or 250 mg twice daily and zidovudine 12 mg/kg/day for 80 weeks new AIDS-defining events was found in 73%, which showed deteriorating health with a mortality rate of 40% (Perry and Noble 1999). Virtually, 'good health' is maintained in all patients using the herbal combination of the present invention shown by the body weight increase, or less than 5% decrease from the starting body weight and with KS of 90–100. This term 'good health' means that all the patients can live a normal life with no complaints and no evidence of disease (KS of 100) or if any, a minor signs and symptoms of disease (KS of 90).

It will be understood that changes may be made within the scope of this invention by one of ordinary skill in the art without departing from the spirit thereof. It is accordingly intended that all matter contained in the above description be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

TABLE 1

Therapeutic effect of botanical combinations ayurvedic composition 3 and ayurvedic composition 4 in maintaining Karnofsky score (KS) of 90–100 in AIDS patients*
On a 100-week noncomparative clinical study (n = 25)

| | | Before Treatment | | | After 100-wk Treatment | | |
|---|---|---|---|---|---|---|---|
| Subject | Sex | Body weight (Kg.) | KS | CD4 count | Body weight (Kg.) | KS | CD4 count |
| 01 | M | 55 | 90 | 143 | 56 | 90 | 210 |
| 02 | M | 45 | 90 | 269 | 48 | 100 | 292 |
| 03 | M | 57 | 90 | 214 | 57 | 90 | 135 |
| 04 | M | 62.5 | 100 | 351 | 71 | 100 | 333 |
| 05 | F | 48 | 100 | 162 | 47 | 100 | 581 |
| 06 | F | 52 | 100 | 176 | 57 | 100 | 401 |
| 07 | M | 64 | 90 | 111 | 66.5 | 100 | 25 |
| 08 | M | 86 | 90 | 392 | 93 | 100 | 555 |
| 09 | F | 48 | 100 | 313 | 52 | 100 | 294 |
| 10 | F | 58 | 90 | 419 | 53 | 100 | 206 |
| 11 | M | 58 | 100 | 497 | 62 | 90 | 589 |
| 12 | F | 45 | 100 | 895 | 49 | 100 | 1097 |
| 13 | F | 55.5 | 90 | 122 | 53.5 | 90 | 81 |
| 14 | F | 43.5 | 90 | 283 | 46.5 | 100 | 565 |
| 15 | F | 41 | 100 | 496 | 43 | 100 | 739 |
| 16 | F | 43 | 100 | 672 | 46 | 100 | 885 |
| 17 | F | 42 | 100 | 646 | 46.5 | 100 | 396 |
| 18 | M | 56 | 100 | 370 | 58 | 100 | 271 |
| 19 | F | 55 | 90 | 137 | 59 | 100 | 129 |
| 20 | F | 39 | 90 | 903 | 42 | 100 | 318 |
| 21 | F | 42 | 100 | 713 | 44 | 100 | 585 |
| 22 | F | 54 | 100 | 535 | 56 | 100 | 398 |
| 23 | F | 56 | 100 | 548 | 56 | 100 | 530 |
| 24 | M | 52 | 90 | 501 | 55 | 100 | 795 |
| 25 | F | 53 | 100 | 249 | 51 | 100 | 232 |

*Patients of full-blown AIDS or HIV-positive confirmed by ELISA and Western Blot assays
Subject 01–13 received one capsule A3 twice daily;
Subject 14–25 received one capsule A3 twice daily plus one capsule A4 twice daily;
Follow-up results (100-week after initiation of treatment) showed all patients remained healthy, free of opportunistic infections (TB, cryptococcal diarrhea, and etc.) no developing AIDS dementia complex or other cerebral events and free of moderate or serious adverse effects commonly observed in antiretroviral therapy, with 0% new AIDS-defining events and 0% mortality rate, vs 73% new AIDS- defining events and 40% mortality rate found in the group treated with didanosine 375 or 250 mg twice daily and zidovudine 12 mg/kg/day for 80 weeks, n = 279 (Perry and Noble 1999).
A3 = ayurvedic composition 3; A4 = ayurvedic composition 4.

What is claimed is:

1. A botanical composition comprising a mixture of dried aqueous or aqueous organic plant extracts in the amounts:

| | |
|---|---|
| Houttuynia cordata | 10–300 mg |
| Combretum quadrangulare | 10–300 mg |
| Mimusops elengi | 10–300 mg |
| Randia siamensis | 10–300 mg |
| Borassus flabellifer | 60–600 mg |
| Total weight of one capsule | 100–1,200 mg | for treating AIDS and immune-deficient pateints to maintain Karnofsky score of 90–100.

2. A botanical composition comprising:
   (i) A kit comprising the composition of claim 1, and
      (ii) a composition consisting of the lyophilized or spray-dried powder of aqueous or aqueous organic solvent extract of plant material Houttuynia cordata in the amount:

| | |
|---|---|
| Houttuynia cordata | 10–500 mg | for treating AIDS and immune-deficient patients to maintain Karnofsky score 90–100.

3. A botanical composition consisting of a mixture of dried aqueous or aqueous organic plant extracts in fixed amounts:

| | |
|---|---|
| Houttuynia cordata | 32 mg |
| Combretum quadrangulare | 20 mg |
| Mimusops elengi | 20 mg |
| Randia siamensis | 20 mg |
| Borassus flabellifer | 308 mg |
| Total weight of one capsule | 400 mg | for treating AIDS and immune-deficient patients to maintain Karnofsky score 90–100.

4. A botanical combination comprises
   (i) A kit comprising the composition of claim 3, and
   (ii) a composition consisting of the lyophilized or spray-dried powder of aqueous or aqueous organic solvent extract of plant material Houttuynia cordata in fixed amount:

| | |
|---|---|
| Houttuynia cordata | 100 mg | for treating AIDS and immune-deficient patients to maintain Karnofsky score of 90–100.

5. A process for preparing botanical compositions for treating AIDS and immune-deficient patients to maintain Karnofsky score of 90–100 comprising washing plant materials Houttuynia cordata, Combretum quadrangulare, Mimusops elengi, Randia siamensis and Borassus flabellifer with water, followed by drying and grinding into powder form each of said botanicals;

said process also includes aqueous or aqueous organic solvent extracting by boiling powder of dried plant materials in water or aqueous organic solvent, filtering, spray-drying the extracts, and mixing the sprayed-dried extracts in the following proportions to to obtain composition, in the form of dried aqueous or aqueous organic extracts in varied amounts:

| | |
|---|---|
| Houttuynia cordata | 10–300 mg |
| Combretum quadrangulare | 10–300 mg |
| Mimusops elengi | 10–300 mg |
| Randia siamensis | 10–300 mg |
| Borassus flabellifer | 60–600 mg |
| Total weight of one capsule | 100–1,200 mg | and preparation of plant material Houttuynia cordata extract by washing, boiling, filtering, lyophilizing, or spray-drying to obtain powder of aqueous or aqueous organic solvent extract of plant material and grinding to obtain a composition in varied amount:

| | |
|---|---|
| Houttuynia cordata | 10–500 mg | wherein said process also includes preparing the pharmaceutical dosage forms of said compositions.

6. Process according to claim 5, wherein
   (i) preparation of a composition consisting of a mixture of dried plant extracts in fixed amounts:

| | |
|---|---|
| Houttuynia cordata | 32 mg |
| Combretum quadrangulare | 20 mg |
| Mimusops elengi | 20 mg |
| Randia siamensis | 20 mg |
| Borassus flabellifer | 308 mg |
| Total weight of one capsule | 400 mg | and (ii) preparation of a composition consisting of washing, boiling, filtering, lyophilizing, or spray-drying to obtain powder of aqueous or aqueous organic solvent extract of plant material and grinding to obtain a composition in fixed amount:

| | |
|---|---|
| Houttuynia cordata | 100 mg |

7. The process according to claim 5, wherein said plant extract mixture and said single botanical drug compositions are filled into hard gelatin capsules as the pharmaceutical dosage form and stored with silica gel bags in air-tight containers protected from light.

8. The process according to claim 5, wherein said pharmaceutical dosage forms of the drugs include dosage forms as syrup or tablet.

* * * * *